United States Patent [19]

Guibert

[11] 4,398,535
[45] Aug. 16, 1983

[54] HYPERTHERMIA TECHNIQUE

[75] Inventor: Raul Guibert, Los Angeles, Calif.

[73] Assignee: Sunset Ltd., Los Angeles, Calif.

[21] Appl. No.: 274,504

[22] Filed: Jun. 16, 1981

Related U.S. Application Data

[63] Continuation-in-part of Ser. No. 97,787, Nov. 27, 1979, Pat. No. 4,307,286.

[51] Int. Cl.³ .............................................. A61F 7/00
[52] U.S. Cl. ................................................. 128/399
[58] Field of Search ..................... 128/38, 39, 40, 24.1, 128/66, 67, 399, 400, 402, 403, 720; 219/400, 369; 34/96, 97; 604/291

[56] References Cited

U.S. PATENT DOCUMENTS

| 2,513,772 | 7/1950 | Amer | 128/67 |
| 3,602,001 | 8/1971 | Bauer | 128/399 |
| 3,894,213 | 7/1975 | Agarwala | 128/400 |
| 3,905,760 | 9/1975 | Johansson et al. | 219/400 |
| 4,133,336 | 1/1979 | Smith | 219/400 |
| 4,331,137 | 5/1982 | Sarui | 128/402 |

FOREIGN PATENT DOCUMENTS

| 490040 | 1/1953 | Canada | 128/66 |
| 1008343 | 5/1957 | Fed. Rep. of Germany | 219/369 |
| 2018468 | 10/1970 | Fed. Rep. of Germany | 128/24.1 |

Primary Examiner—Kyle L. Howell
Assistant Examiner—Max F. Hindenburg
Attorney, Agent, or Firm—Michael Ebert

[57] ABSTRACT

A heat therapy technique by which heat is applied to a limited skin area of a patient to penetrate the tissue and produce hyperthermia in an internal region underlying this area without, however, causing undue discomfort to the patient or damaging surface tissue. Applied to the skin area is heated air in a pulsatory air wave pattern whose relatively brief pulses flow at high velocity and are at a high temperature well above body temperature and whose static intervals between pulses are at a medium temperature somewhat above body temperature. As a consequence, heat transfer from the surface tissue toward the internal region takes place during the intervals, thereby reducing the temperature of the surface tissue and preventing it from reaching an unacceptable level despite the high temperature of the high-velocity pulses applied thereto.

12 Claims, 5 Drawing Figures

HYPERTHERMIA TECHNIQUE

RELATED APPLICATIONS

This application is a continuation-in-part of my copending application Ser. No. 097,787, filed Nov. 27, 1979, now U.S. Pat. No. 4,307,286 which in turn relates back to the earlier-filed applications identified in this patent.

BACKGROUND OF INVENTION

This invention relates generally to techniques for the hyperthermia treatment of living tissue, and more particularly to devices for applying hot-air, high-velocity pulses to a limited skin area of the body in a manner which acts to significantly raise the temperature of an internal region underlying the skin area without excessively heating surface tissue.

The interior of the human body has a normal temperature level which is usually said to be 98.6° F. But actually, in the course of each 24-hour period, the body temperature rises above and falls below this nominal value within a 1.8° F. range. Body temperature is determined by the relationship existing between the amount of heat internally generated, which depends on basal metabolism, and the amount of heat escaping from the body. Additional heat is produced as a result of muscular activity, this being dissipated by an increase in radiation, conduction or evaporation from the skin surface and by more rapid and deep breathing.

Thus the skin is the interface between the internally heated body and the atmosphere, and is in heat exchange relationship therewith. If the heat produced by a body surpasses heat losses therefrom, this gives rise to fever; but if heat losses exceed heat production, then the body temperature falls below the nominal value, resulting in shivering and hypothermia.

Medical practitioners since ancient times have known that the application of heat to the body is useful in the relief of muscle soreness and various aches and pains, as well as in the treatment of certain abnormalities. Thus the application of heat for the treatment of arthritis and other abnormal conditions is commonplace. Hot water bottles and electrical heating pads are in widespread use not merely to provide warmth, but also to afford a degree of relief or therapy for various conditions. Heat is also used medically in the resolution of infected areas.

While the present invention is generally applicable to all abnormal conditions which can be benefited by the application of heat to the surface of the body, it will now be considered in the context of malignant tumor treatment. It is recognized that by heating tumors to a higher temperature than the surrounding tissue, the tumor may be caused to shrink and disappear. As noted in *The New York Times* of April 14, 1981 (section C2) in an article on modern approaches to cancer treatment, the effectiveness of heat therapy is based on the fact that cancers have poor circulation and a reduced ability to dissipate heat. "Thus a temperature of more than 113 degrees Fahrenheit could destory cancer cells while sparing normal tissue."

Patients with tumors in their arms and legs have been treated by a perfusion therethrough of hot blood, and tumors in bladders have been treated by flushing the organ with hot fluid. It has also been known to immerse patients in hot wax, and in some cases, medical practitioners have gone so far as to elevate the body temperature of patients by infecting them with malaria.

These known hyperthermia techniques, as well as those based on the use of microwave, high-frequency radiation and thermoelectric techniques are described in some detail in the U.S. patents to Sterzer, Nos. 4,190,053; Gordon, 4,106,488; Whalley, 4,121,592; Doss, 4,016,886; Bender, 4,186,294 and Ulrich, 3,618,590.

Difficulty has heretofore been experienced in applying heat to a patient which is electrically or otherwise generated. When transferring heat through living tissue to a site underlying the skin, if the heat applied to the skin surface is within a tolerable temperature range, then not enough heat energy is transferred to the site to afford beneficial effects. When, however, the skin temperature of the applied heat is such as to bring about an adequate heat transfer to the internal site, then the skin temperature is usually above an acceptable level, and this may result in extreme discomfort to the patient and even to the burning of surface tissue. The same problem is encountered when using high-frequency radio heating; for, as pointed out in the above-identified Whalley patent, in many cases such treatment results in damage to the skin.

In my above-identified U.S. Pat. No. 4,307,286, apparatus is disclosed whereby cold, pre-cooked packaged meals may be rapidly heated to a service temperature level without causing destructive re-cooking of the meals. To this end, applied to the package is a stream of heated air in a pulsatory thermal wave pattern whose pulses are at a temperature well above the service temperature level and whose intervals between pulses are at a lower temperature. As a result of this thermal wave pattern, heat is transferred from the surface of the food body to the interior thereof during the lower temperature intervals, thereby preventing the surface temperature from rising above the service temperature level despite the fact that it is subjected to high temperature pulses.

In the present invention, this pulsatory thermal wave pattern is exploited to carry out heat therapy on patients without injury to surface tissue. While the invention will be described mainly in connection with therapy produced by hyperthermia, the same principles are applicable to hypothermia treatment, in which therapeutic effects are produced by cooling an internal body site.

SUMMARY OF INVENTION

In view of the foregoing, the main object of this invention is to provide a method and apparatus which makes effective high temperature heat therapy feasible without inflicting injury to the surface tissue in the area where the heat is applied and without causing undue discomfort to the patient.

It must be borne in mind that when heat is applied to a skin area at a temperature which is significantly greater than body temperature, some unavoidable degree of discomfort will be experienced, and that the concern of the present invention is to keep such discomfort within a tolerable range and to avoid any damage to surface tissue.

More particularly, an object of this invention is to provide a technique which applies a stream of heated air to a limited skin area to effect heat transfer to an internal region underlying this area to cause the temperature of the region to rise to a level appropriate to hyperthermia treatment without giving rise to an excessive temperature damaging to the surface tissue.

Yet another object of this invention is to provide an apparatus which includes an applicator in the form of a flexible heating pad which is adapted to conform to a body area to be heated.

Also an object of the invention is to provide an efficient and reliable heat therapy instrument which is easy and safe to operate and which may be manufactured at relatively low cost.

Briefly stated, these objects are attained in a heat therapy technique by which heat is applied to a limited skin area of a patient to penetrate the tissue to produce hyperthermia in an internal region underlying this area without, however, causing undue discomfort to the patient or damaging surface tissue. Applied to the skin area is heated air in a pulsatory air wave pattern whose relatively brief pulses flow at high velocity and are at a high temperature well above body temperature and whose static intervals between pulses are at a medium temperature.

As a consequence, heat transferred from the surface tissue toward the internal region takes place during the intervals, thereby reducing the temperature of the surface tissue and preventing it from reaching an unacceptable level despite the high temperature of the high-velocity pulses applied thereto.

OUTLINE OF DRAWINGS

For a better understanding of the invention as well as other objects and further features thereof, reference is made to the following detailed description to be read in conjunction with the accompanying drawings, wherein:

FIG. 1 is a schematic representation of a preferred embodiment of a heat therapy device in accordance with the invention;

FIG. 2 separately illustrates, in perspective, the applicator included in the device;

DESCRIPTION OF INVENTION

First Embodiment

Figure 1:
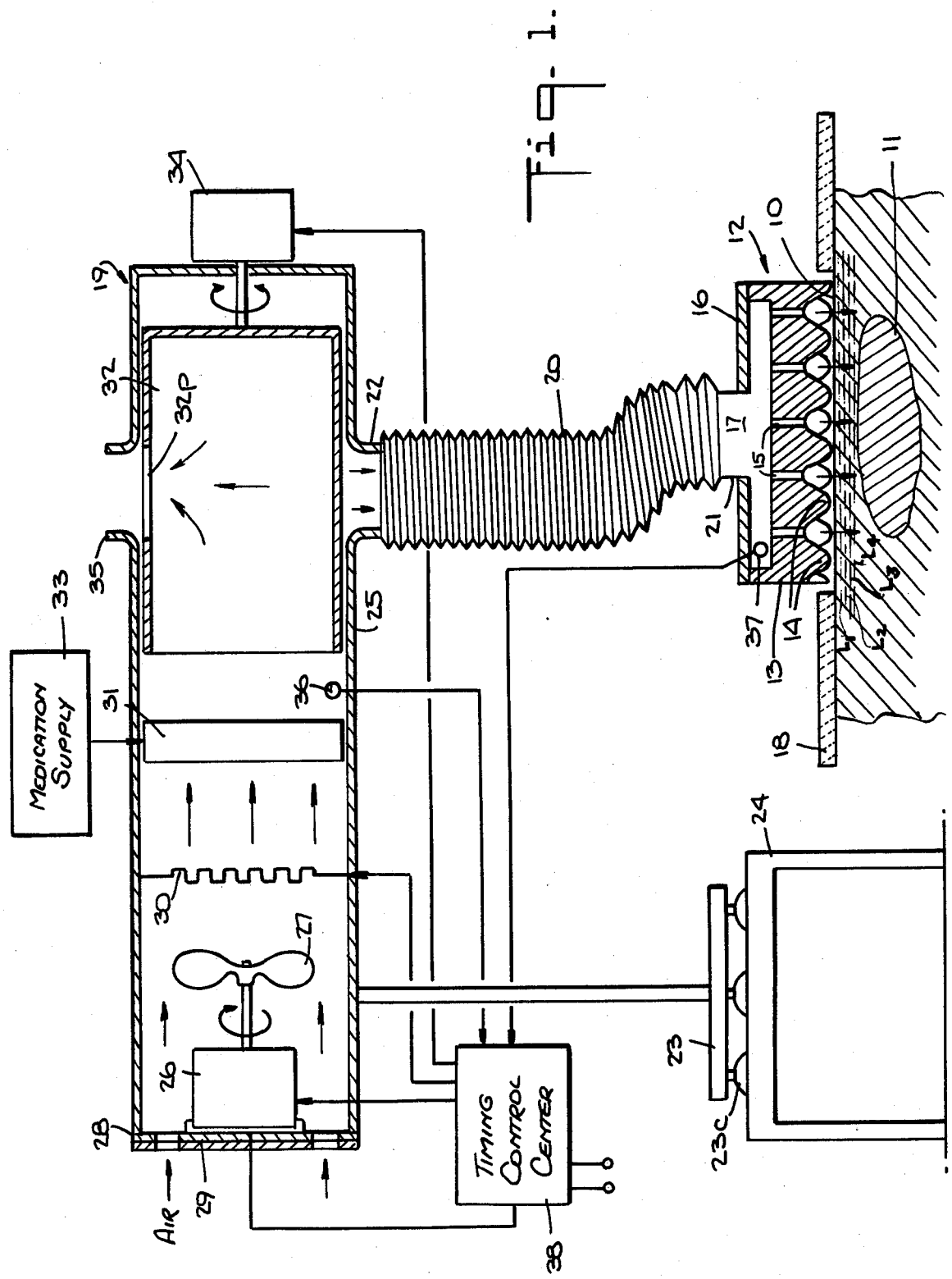
Figure 2:
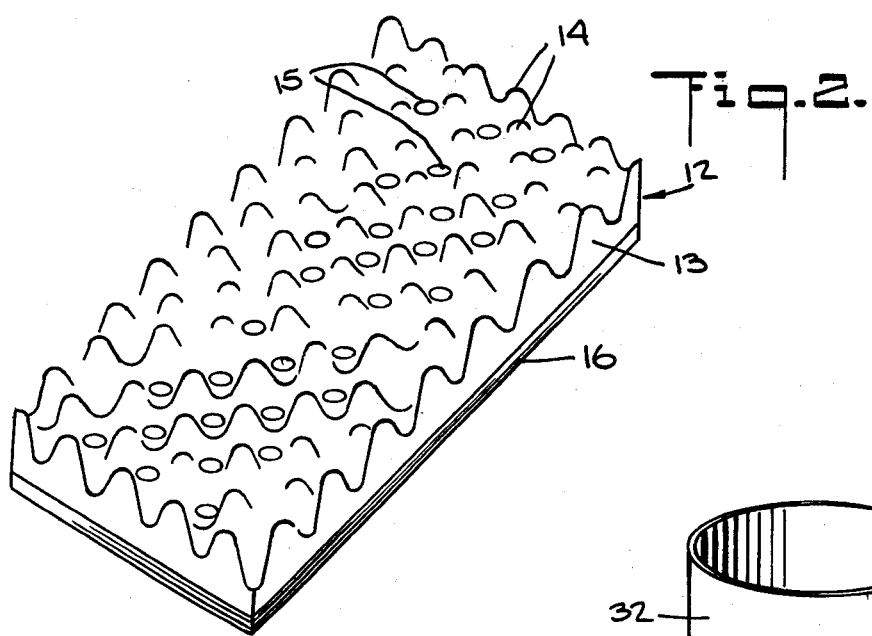
Figure 3:
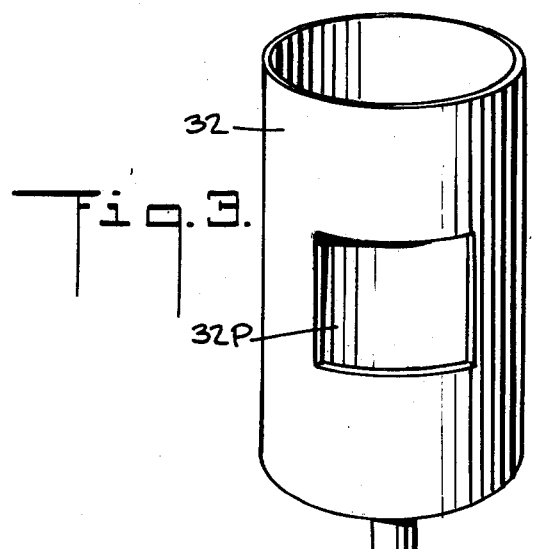
FIG. 3 is a perspective view of the valve included in the device.
Figure 4:
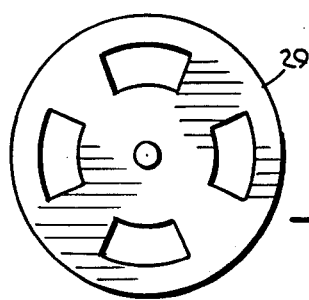
FIG. 4 is a plan view of one of the inlet shutter elements.

Referring now to FIG. 1, there is shown a heat therapy device for applying heat to the skin surface 10 of a patient in order to subject an internal tumor 11 to hyperthermia treatment, the tumor lying in a region underlying the area of the skin subjected to the heat generated in the device.

The device includes an applicator, generally designated by numeral 12, which is constituted by a rectangular pad 13 formed of synthetic flexible foam material such as polyurethane or PVC whose outer face is molded to define a staggered array of projecting fingers 14 and an array of outlets 15 interspersed between the fingers in the troughs formed thereby. The inner face of the pad is indented to define a shallow well closed by a cover plate 16 to form an internal chamber 17.

When in use, the projecting fingers 14 rest on the skin while heated air is emitted from outlets 15 at high velocity, to uniformly heat the underlying skin area. The application of heat is confined to this skin area by a thermal blanket 18 having an opening to accommodate the applicator. In practice, the skin area being treated may be protectively coated with Vaseline, silicone oil or other preparation having protective properties.

Applicator 12 is coupled to a pulsatory heat generator, generally designated by numeral 19, by means of a flexible pipe 20, one end of which communicates with the inlet port 21 of the applicator, the other end communicating with the outlet port 22 of the heat generator.

Heat generator 19 is supported by means of a suitable stand 23, such as one having suction cups 23 C on its base, on a table 24. Generator 19 is provided with a cylindrical casing 25 having a motor 26 mounted therein at one end, the motor driving a fan 27. The fan acts to draw ambient air into the casing through an adjustable shutter composed of a fixed disc 28 having a circular series of slots therein and a rotatable disc 29 having a similar slotted formation, the maximum opening being when the slots in the two discs are in exact registration and the minimum when the slots are altogether out of registration.

Ambient air drawn into casing 25 by fan 27 is blown through an electrical heater element 30, the hot air being forced through a fibrous or sponge-like replaceable air filter 31 into a cylindrical valve 32. In practice, filter 31 may be continuously saturated with a liquid medicant fed thereto at a controlled rate from a supply 33.

Valve 32 is provided with a port 32P and is oscillated about its axis by a reciprocating motor 34, such that port 32P is alternately in registration with outlet 22 coupled to applicator pipe 20 or with an outlet 35 whose position is diametrically opposed to outlet 22, the heated air being discharged into the atmosphere through outlet 35.

The temperature of air passing out of air filter 31 is sensed by a thermistor or other form of detector 36, while the temperature of the air in applicator chamber 17 is sensed by a similar detector 37. The detected signals are applied to an electronic timing and control center 38 which acts to adjust and control the parameters of the heat generator 19 to provide and maintain the desired pulsatory wave pattern.

Control center 38 includes a manually-settable timer to activate the heat generator for a desired period, such as a half hour, or any other appropriate period. The relative durations of the pulses and intervals are also adjustable so that, for example, each pulse may last 4 seconds and each interval 7 seconds. Detector 36, which senses the temperature of the air fed into valve 32, acts in conjunction with the control center to thermostatically regulate heater 30 to maintain a desired temperature level. Detector 36, which senses the heat within casing 25, acts in conjunction with the control center to regulate shutter 29 to adjust the air input opening thereof to provide the desired air temperature for the skin.

In practice, the control may be manual, in which case means are provided to indicate the applicator temperature, and the operator then turns the shutter to provide incoming air resulting in a diresed temperature level and turns a potentiometer coupled to the heater to adjust the heater temperature.

In order to render the generator useful for hypothermia, element 30 may be of the thermoelectric type capable of selectively providing either a reduced temperature or an elevated temperature. Such thermoelectric elements make use of dissimilar metals and replace the mechanics of conventional refrigeration when operating in the cold mode. Thus when the generator is operative in the hyperthermia mode, air drawn into the casing is heated and blown at high velocity into valve 32 which alternately feeds the air into the applicator and into the atmosphere; and when the generator is operative in the hypothermia mode, the air drawn into the casing is cooled and blown at high velocity into valve 32 to produce in the applicator pulses of cold air.

Operation

Figure 5:
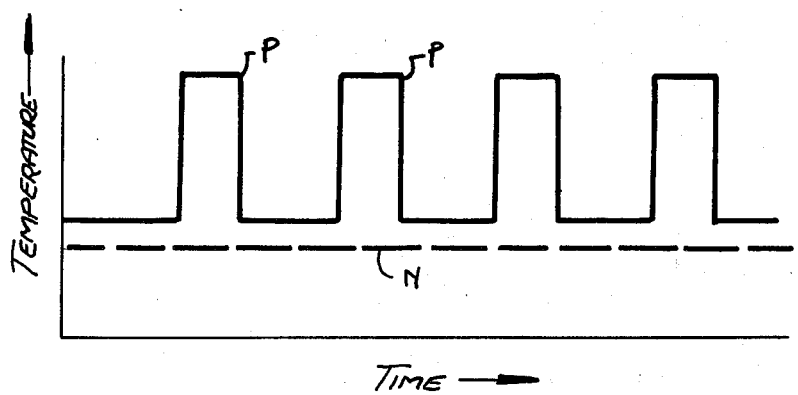
FIG. 5 is a graph showing the pulsatory wave generated by the device.

Normal body temperature is 98.6° F., this level being indicated in FIG. 5 by horizontal line N. The pulsatory thermal wave pattern is above line N and is constituted by periodic pulses P at a high temperature of, say, 150° F. and higher, and no-flow or static intervals between pulses at a medium temperature somewhat above body temperature, such as 110.0° to 120° F. Because the high temperature air flows over the skin area at high velocity during the pulses, this forced convection results in a rapid heat exchange. And while the small volume of air in the confined skin area during the static intervals has a very low thermal capacity, its temperature because of residual heat in the applicator is somewhat above skin temperature.

The rate of pulsing is a crucial aspect of the invention, for the body region containing tumor 11 is formed of living tissue having relatively poor heat conductivity and is composed effectively of a succession of layers, beginning with the surface or skin layer $L_1$ and going through layers $L_2$ etc. into the tumor. The tumor can be heated to a hyperthermia level above body temperature, say, to 115° F. and above, only by transmitting heat through the successive layers of poor thermal conductivity.

As noted in the article "Heat Therapy for Cancer" in *Discover*, June 1981, published by Time, Inc., because the circulation in tumors is poor, the blood moves sluggishly therein and does not carry away heat as rapidly as it does in ordinary tissue. Thus a tumor can be heated to a lethal temperature of over 110° F. while the tissue in the region between the tumor and skin remains at a safe, lower temperature. Tumor cells are apparently more sensitive to heat than normal cells and seem to have a higher metabolism; hence tumor cells are more easily overstressed by heat. While the question of whether cancerous cells have a greater sensitivity than normal cells remains controversial, there is little argument about the lethal effect of heat on tumors.

Outer layer $L_1$ is initially at 98.6° F. Assuming that each high temperature pulse period lasts 3 seconds followed by a five-second lower temperature interval, and that the first 180° F. pulse flowing past the skin area at high velocity for three seconds acts to raise the temperature of the first layer $L_1$ to 104° F., then during the 110° F. interval which follows, heat from outer layer $L_1$ will be transferred inwardly to second layer $L_2$ which is thereby raised in temperature to, say, 100° F. with a resultant reduction in the temperature of the outer layer to, say, 102° F.

Thus the interval between the hot air pulses represents a relaxation period during which heat transfer takes place from the outside in, but not from the inside out; for the temperature outside the skin is always above the body temperature. When outer layer $L_1$, now at 102° F., is again subjected to the next hot air high velocity pulse at 180° F., this will raise the temperature of the outer layer another notch, and the temperature of this layer will again be somewhat reduced during the interval which follows when heat is transferred from outer layer $L_1$ to the next layer $L_2$.

It is important to bear in mind that a small volume of air has a low thermal capacity, and that because of the high velocity of the pulses, a larger volume of air is brought into heat exchange relationship with the skin during the pulse period, whereas in the interval, it is only a small volume of air.

Similar heat transfer actions take place concurrently between the second and third layers $L_2$ and $L_3$ and between the third and fourth layers $L_3$ and $L_4$ and so on toward the tumor region, very much in the fashion of an electronic cascade counter in which when an input signal (heat pulse) is received, the state of each stage (layer) in the cascade is advanced in an ordered sequence.

Thus the intervals between hot air pulses applied to the surface layer of the body allows time for transfer of heat to take place from layer to layer; and because outer layer $L_1$ is permitted to cool down during these intervals, the temperature of the outer layer is never permitted to rise to an execessive level, even when the tumor is heated to an effective hyperthermia temperature of above 115° F. And while the tissue between the tumor and the skin is also caused to rise in temperature, the cooling effect of the circulatory system prevents this tissue from being overheated.

The heating applicator may be used in those medical applications which benefit from the use of conventional heating hot water bottles or heater pads, the advantage of the present pad being that it is possible to transfer more heat into the body without, however, undue discomfort to the patient or damage to his skin.

While there have been shown and described preferred embodiments of a hyperthermia technique in accordance with the invention, it will be appreciated that many changes and modifications may be made therein without, however, departing from the essential spirit thereof. Thus while a particular form of heat or cold generator has been disclosed herein operating in conjunction with a particular form of applicator, in practice any of the pulsed wave sources disclosed in the above-identified copending application may be used for the generator. And the applicator may take other forms and need not be constituted by a foam plastic pad.

I claim:

1. A thermal therapy device for a living organism having a normal body temperature, the device serving to raise the temperature of a region underlying the body skin to a hyperthermia level having beneficial effects, said device comprising:

A. a source including a heater and means operating in conjunction with the heater for generating a pulsatory air wave constituted by periodic pulses having a predetermined duration flowing at high velocity and having a high temperature well above said normal body temperature, and means providing relatively static intervals between said periodic pulses thereby creating a medium temperature somewhat above said normal temperature at the site of application; and B. an applicator coupled to said source to apply said pulsatory wave to a limited skin area of the body to thermally penetrate the tissue to cause the region thereunder to rise in temperature to said hyperthermia level without injury to surface tissue, rapid heat transfer taking place from the air to the surface layer of the skin area during said pulses, the intervals in said wave having a duration relative to that of said pulses whereby heat transfer inwardly from the surface layer of the tissue takes place during said intervals to cause a reduction in the temperature of the surface layer sufficient to prevent excessive heating thereof.

2. A device as set forth in claim 1, wherein said heater is adjusted to produce a pulsatory wave in which the pulse high temperature is above 150° F. and the interval medium temperature is no higher than 120° F.

3. A device as set forth in claim 1, wherein said applicator is constituted by a pad of flexible foam plastic material having an inner chamber coupled to said source and having openings between said chamber and the outer face of the pad.

4. A device as set forth in claim 3, wherein said outer face is formed with an array of projecting fingers which engage the skin.

5. A device as set forth in claim 1, wherein said source includes a cylindrical casing having at one end a motor-driven fan therein which flows air drawn from the atmosphere through a heater element toward an oscillating valve provided with a port which alternately registers with diametrically-opposed outlets in said casing, one outlet being coupled to said applicator, the other to the atmosphere.

6. A device as set forth in claim 5, wherein the casing is provided at said one end with an adjustable shutter to set the amount of atmospheric air admitted into the casing.

7. A device as set forth in claim 5, further including an air filter interposed between the heater and the valve.

8. A device as set forth in claim 7, further including means to supply a liquid medicant to the filter.

9. A device as set forth in claim 5, wherein said heater element is a thermoelectric element formed of dissimilar metals which is also operable to produce a reduced temperature whereby the generator is also usable for hypothermia treatment.

10. A device as set forth in claim 1 wherein said means are arranged to produce a pulsatory wave whose pulses each have a duration of about three seconds and whose intervals each have a duration of about five seconds.

11. A thermal therapy device for a living organism having a normal body temperature level, the device serving to raise the internal temperature in a region underlying a limited skin area of the body to a hyperthermia level having beneficial effects, said device comprising:
A. a source of air heated to an elevated temperature level well above said normal level and
B. means to flow heated air derived from said source at high velocity across the surface layer of said limited skin area in a pulsatory wave pattern to thermally penetrate the tissue thereof to cause the region thereunder to rise in temperature to said hyperthermia level without injuring the tissue of the surface layer in a manner whereby the surface is subjected periodically to a pulse of said heated air flowing at high velocity to cause rapid heat transfer from the air to the surface layer, and means providing a relatively static interval between said pulses in which the air temperature is at a level intermediate said elevated and said normal level, said interval having a duration relative to that of said pulse during which heat transfer which then takes place inwardly in the course of said interval from the surface layer toward said region causes a reduction in the temperature of the surface layer which is sufficient to prevent excessive heating and damage to said surface layer, said intermediate level preventing heat transfer outwardly from said surface layer to the air during said interval.

12. The method of raising the temperature of a region underlying a limited skin area of the body of a living organism having normal body temperature to a hyperthermia level having beneficial effects, said method comprising the steps of:
A. heating air to an elevated temperature level well above the normal body temperature; and
B. flowing the heated air at high velocity across the surface of the limited skin in a pulsatory wave pattern whereby the surface is subjected periodically to a pulse of heated air flowing at high velocity to cause rapid heat transfer from the air to the surface layer of the skin followed by a relatively static interval in which the air temperature is at a level intermediate said elevated and said normal level, said interval having a duration relative to that of said pulse during which heat transfer which then takes place inwardly in the course of the interval from the surface layer toward said region causes a reduction in the temperature of the surface layer sufficient to prevent excessive heating and damage to said surface layer, said intermediate level preventing heat transfer outwardly from said surface layer to the air during said interval.

* * * * *